(12) United States Patent
Lobdell et al.

(10) Patent No.: US 6,868,720 B2
(45) Date of Patent: Mar. 22, 2005

(54) TESTING OF PRESSURE SENSOR IN SURGICAL CASSETTE

(75) Inventors: Donn D. Lobdell, Sunol, CA (US); Michael D. Morgan, Costa Mesa, CA (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 10/376,499

(22) Filed: Feb. 28, 2003

(65) Prior Publication Data

US 2004/0074281 A1 Apr. 22, 2004

Related U.S. Application Data

(60) Provisional application No. 60/419,062, filed on Oct. 16, 2002.

(51) Int. Cl.[7] .................................................. G01B 5/16
(52) U.S. Cl. ........................... 73/157; 73/157; 73/701; 73/718; 73/745; 600/488; 604/122
(58) Field of Search .......................... 73/157, 701, 718, 73/745; 600/488; 604/122

(56) References Cited

U.S. PATENT DOCUMENTS

| | | |
|---|---|---|
| 526,917 A | 10/1894 | Cochran |
| 1,718,494 A | 6/1929 | Schurig |
| 2,260,837 A | 10/1941 | Kuehni |
| 2,510,073 A | 6/1950 | Clark |
| 2,583,941 A | 1/1952 | Gordon |
| 3,805,617 A | 4/1974 | Kamazuka |
| 4,192,191 A | 3/1980 | Nelson |
| 4,281,666 A | 8/1981 | Cosman |
| 4,281,667 A | 8/1981 | Cosman |
| 4,452,202 A | 6/1984 | Meyer |
| 4,505,157 A | 3/1985 | Hong Le |
| 4,539,849 A | 9/1985 | Pike |
| 4,541,283 A | 9/1985 | Stuhlmann |
| 4,653,508 A | 3/1987 | Cosman |
| 4,755,669 A | 7/1988 | Grant et al. |
| 4,886,070 A | 12/1989 | Demarest |
| 4,892,985 A | 1/1990 | Tateishi |
| RE33,360 E | 10/1990 | Reynolds et al. |
| RE33,518 E | 1/1991 | McCord et al. |
| 5,029,478 A | 7/1991 | Wamstad |
| 5,080,098 A | 1/1992 | Willett et al. |
| 5,095,401 A | 3/1992 | Zavracky et al. |
| 5,144,843 A | 9/1992 | Tamura et al. |
| 5,257,630 A | 11/1993 | Broitman et al. |
| 5,275,053 A | 1/1994 | Wlodarczyk et al. |
| 5,333,504 A | 8/1994 | Lutz et al. |
| 5,353,633 A | 10/1994 | Benedikt et al. |
| 5,392,653 A | 2/1995 | Zanger et al. |

(List continued on next page.)

FOREIGN PATENT DOCUMENTS

| | | |
|---|---|---|
| EP | 0 579 504 | 1/1994 |
| EP | 1 258 717 | 11/2002 |
| WO | WO 88/04042 | 6/1988 |
| WO | WO 93/24817 | 9/1993 |
| WO | WO 00/44415 | 8/2000 |

OTHER PUBLICATIONS

Lebow® Load Cell and Torque Sensor handbook, pp. 63–99 (1989).

Primary Examiner—Hezron Williams
Assistant Examiner—André K. Jackson
(74) Attorney, Agent, or Firm—W. David Lee

(57) ABSTRACT

A method of determining the accuracy of a pressure sensor in a surgical cassette is disclosed. The method involves displacing a diaphragm of the sensor a pre-defined amount of displacement, and measuring the force exerted on the diaphragm by the displacing step. The accuracy of the pressure sensor is determined by comparing the force measured in the measuring step to a pre-defined force for the pre-defined amount of displacement.

5 Claims, 3 Drawing Sheets

U.S. PATENT DOCUMENTS

| | | |
|---|---|---|
| 5,460,049 A | 10/1995 | Kirsch |
| 5,460,490 A | 10/1995 | Carr et al. |
| 5,470,312 A | 11/1995 | Zanger et al. |
| 5,528,214 A | 6/1996 | Koga et al. |
| 5,583,297 A | 12/1996 | Stocker et al. |
| 5,661,245 A | 8/1997 | Svoboda et al. |
| 5,699,934 A * | 12/1997 | Kolcun et al. ............... 222/1 |
| 5,752,918 A | 5/1998 | Fowler et al. |
| 5,848,971 A | 12/1998 | Fowler et al. |
| 5,866,822 A | 2/1999 | Willig |
| 5,880,373 A | 3/1999 | Barton |
| 5,910,110 A | 6/1999 | Bastable |
| 6,058,779 A | 5/2000 | Cole |
| 6,293,926 B1 | 9/2001 | Sorensen et al. |
| 2001/0004684 A1 | 6/2001 | Morgan et al. |

* cited by examiner

TESTING OF PRESSURE SENSOR IN SURGICAL CASSETTE

This application claims the priority of U.S. Provisional Application No. 60/419,062 filed Oct. 16, 2002.

FIELD OF THE INVENTION

This invention relates generally to pressure sensors used on surgical cassettes and more particularly to a method of testing the accuracy of such sensors prior to surgery.

DESCRIPTION OF THE RELATED ART

Surgical cassettes utilized in phacoemsulsification, vitreoretinal, or other ophthalmic surgical procedures typically have an aspiration manifold within the cassette. When the cassette is inserted into an ophthalmic surgical console, the aspiration manifold is operatively coupled to a source of vacuum. The cassette is also fluidly coupled to the aspiration port of an ophthalmic surgical handpiece, typically via flexible plastic tubing. Ophthalmic tissue is aspirated by the handpiece into a collection bag that is also fluidly coupled to the aspiration manifold of the cassette. Such cassettes typically employ a variety of pressure sensors to measure the vacuum level within the aspiration manifold of the cassette and thus the eye. For example, such cassettes have utilized both conventional vacuum transducers and non-invasive pressure sensors to measure such vacuum. Exemplary non-invasive pressure sensors are disclosed in U.S. Pat. Nos. 5,910,110 to Bastable and 5,470,312 to Zanger et al., both of which are incorporated herein in their entirety by reference.

Communicating an accurate reading of the vacuum level within the aspiration manifold of such surgical cassettes to the surgeon is critical to the success of the surgical procedure and the safety of the patient. For example, during a phacoemulsification procedure, the tip of the phacoemulsification handpiece may become occluded with ophthalmic tissue. When the tip occludes, the peristaltic pump vacuum source of the surgical system continues to pump, increasing the vacuum within the aspiration line of the handpiece. When the blockage on the tip is removed, the patient's eye may be exposed to a dangerous surge of vacuum. However, if the vacuum level within the aspiration manifold of the cassette is measured and provided to the surgeon, the surgeon can use the user interface of the surgical console to slow down or stop the peristaltic pump to bring the vacuum to the desired level before the blockage breaks free. To insure that an accurate aspiration manifold vacuum reading is provided to the surgeon, certain ophthalmic surgical systems utilize two pressure sensors to measure vacuum in the aspiration manifold of the cassette. With this design, the surgeon still receives an accurate measurement of the vacuum level within the aspiration manifold of the cassette even if one of the sensors fails or is not working properly. However, such dual redundancy increases the cost and complexity of the surgical system and cassette. Therefore, a need exists for an improved apparatus and method of insuring the accuracy of such pressure sensors.

SUMMARY OF THE INVENTION

The present invention is directed to a method of determining the accuracy of a pressure sensor in a surgical cassette. A surgical cassette having a pressure sensor is provided. The pressure sensor has a diaphragm. A surgical console with a cassette receiving area is also provided. The cassette is disposed in the cassette receiving area. The diaphragm is displaced a pre-defined amount of displacement, and the force exerted on the diaphragm by the displacing step is measured. The accuracy of the pressure sensor is determined by comparing the force measured in the measuring step to a pre-defined force for the pre-defined amount of displacement.

BRIEF DESCRIPTION OF THE DRAWINGS

For a more complete understanding of the present invention, and for further objects and advantages thereof, reference is made to the following description taken in conjunction with the accompanying drawings in which.

DETAILED DESCRIPTION OF THE PREFERRED EMBODIMENTS

The preferred embodiments of the present invention and their advantages are best understood by referring to FIGS. 1–5 of the drawings, like numerals being used for like and corresponding parts of the various drawings.

Figure 1:
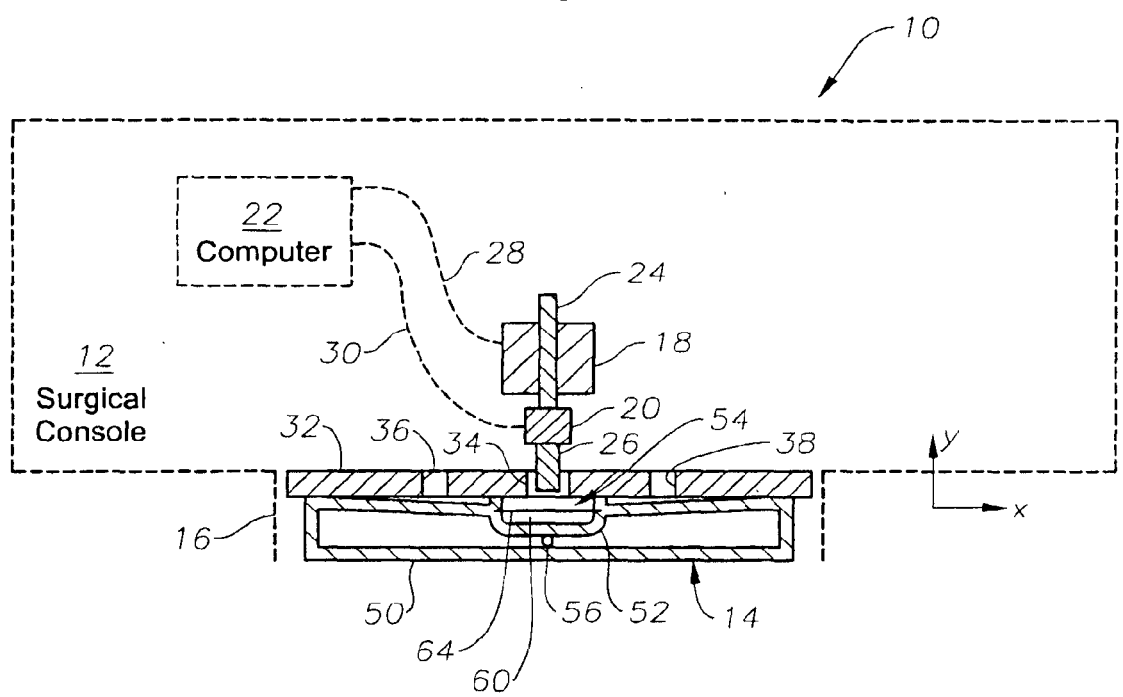
FIG. 1 is a top, partially sectional view schematically illustrating the relevant portions of a surgical system and cassette according to a preferred embodiment of the present invention.
Figure 2:
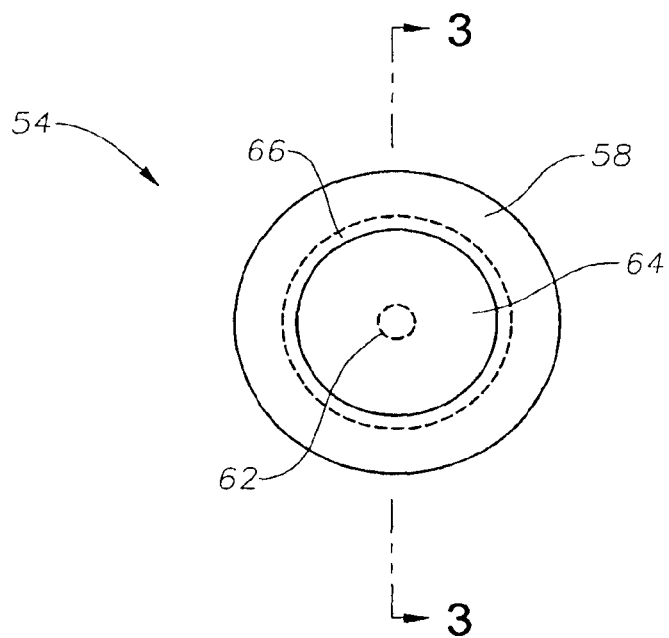
FIG. 2 is a front view of the non-invasive pressure sensor of the surgical cassette of FIG. 1 according to a preferred embodiment of the present invention.
Figure 3:
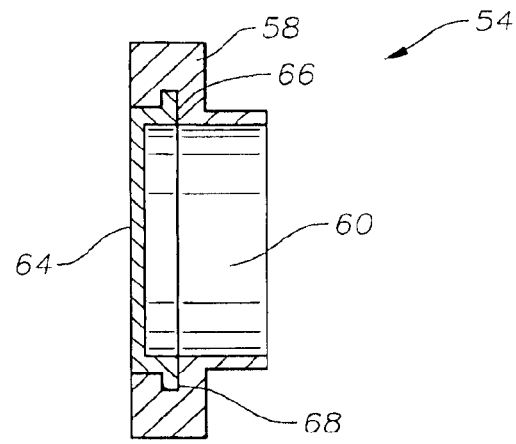
FIG. 3 is a side, sectional view of the sensor of FIG. 2 along line 3—3.

Referring to FIGS. 1–3, a surgical system 10 generally includes a surgical console 12 and a surgical cassette 14. Console 12 and cassette 14 are preferably for use in ophthalmic surgery, although the present invention is applicable to other surgical systems that provide aspiration to a surgical handpiece. Surgical console 12 includes a cassette receiving area 16 for removably receiving cassette 14, a linear actuator 18, a load cell or force gage 20, and a computer or microprocessor 22. Linear actuator 18 includes a lead screw 24 having a plunger 26 on one end. Linear actuator 18 is preferably a conventional linear stepper motor having a shaft 24. A preferred linear stepper motor 18 is the Model ZB17GBKR-13 available from Eastern Air Devices (EAD) of Dover, N.H. The rotation of linear stepper motor 18 one step preferably results in a 0.0003125 inch linear displacement of shaft 24 and plunger 26. However, linear actuator 18 may also be a DC motor with position feedback, a pneumatically actuated piston, or other conventional means of moving a plunger with a known displacement. A preferred load cell for load cell 20 is the Model 31 available from Sensotec of Columbus, Ohio. Linear stepper motor 18 and load cell 20 are electronically coupled to computer 22 in a conventional manner, as schematically illustrated by lines 28 and 30, respectively. Cassette receiving area 16 has a front plate 32 for interfacing with cassette 14 including an aperture 34 for plunger 26 and apertures 36 and 38 for other plungers of console 12 used to interface with various portions of cassette 14.

Surgical cassette 14 generally includes a body 50 having a pressure sensor receiving area 52, a non-invasive pressure sensor 54 disposed in receiving area 52, and an aspiration manifold 56 fluidly coupled to sensor 54. Body 50 is preferably a rigid thermoplastic and may be made from any suitable method, such as machining or injection molding. Although not shown if the Figures, cassette 14 may also include additional fluid channels, manifolds, or ports that provide control of aspiration or irrigation fluid. A preferred ophthalmic surgical cassette for cassette 14 is disclosed in U.S. Pat. No. 6,293,926, which is incorporated herein in its entirety by this reference.

Pressure sensor 54 has a body 58 having a cavity 60, a port 62 for fluidly coupling with aspiration manifold 56, and a diaphragm or membrane 64. Body 58 is preferably a rigid thermoplastic, and diaphragm 64 is preferably made of stainless steel. Diaphragm 64 has a rim 66 that mates with a recess 68 in body 58 to retain diaphragm 64 within body 58. Diaphragm 64 preferably has a diameter of about 0.996 inches (not including rim 66). Diaphragm 64 preferably has a thickness of about 0.0027 inches to about 0.0033 inches, and most preferably about 0.003 inches. Diaphragm 64 is preferably made of 17-7 stainless steel.

Figure 4:
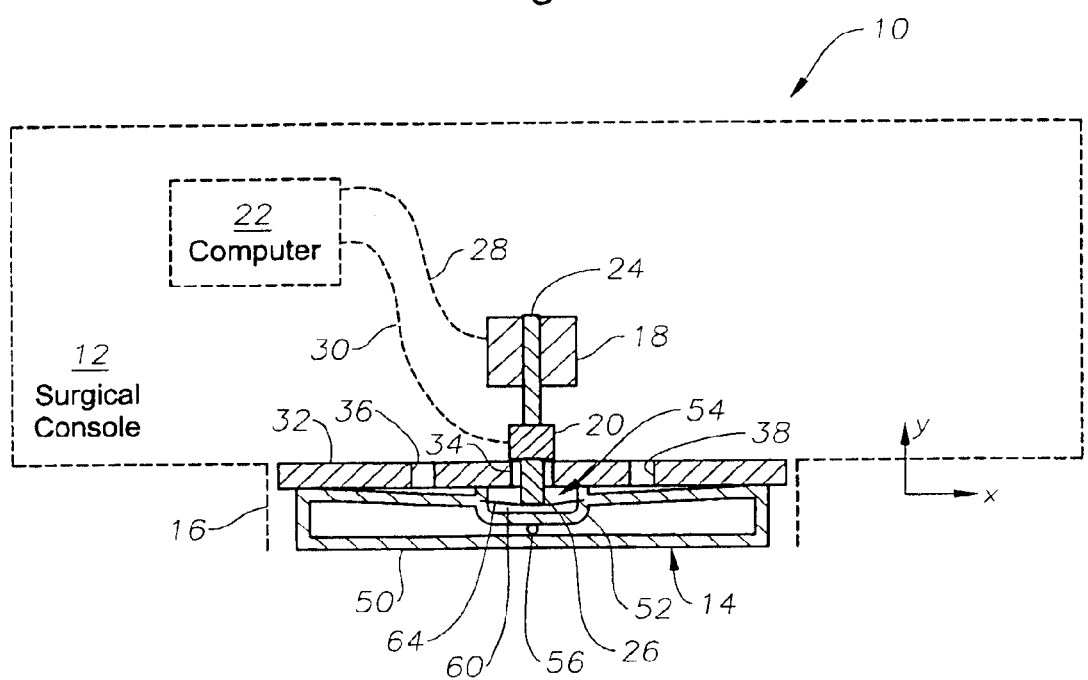
FIG. 4 is a top, partially sectional view similar to FIG. 1 showing the plunger of the surgical system loading the diaphragm of the sensor of FIGS. 2–3.

When cassette 14 is inserted into cassette receiving area 16 of console 12, computer 22 rotates stepper motor 18, causing shaft 24 and plunger 26 to be moved linearly through aperture 34 toward diaphragm 64 of sensor 54. Stepper motor 18 moves plunger 26 until it contacts and displaces diaphragm 64, as shown in FIG. 4. Plunger 26 preferably displaces diaphragm 64 until a known pre-load force ("$F_{preload}$") is placed on diaphragm 64 as measured by load cell 20. $F_{preload}$ must be greater than the largest vacuum exerted on diaphragm 64 via aspiration manifold 56 of cassette 14 and cavity 60 of sensor 54. $F_{preload}$ for diaphragm 64 is preferably about 4.0 $lb_f$.

When console 12 provides vacuum to aspiration manifold 56 of cassette 14 and thus cavity 60 of sensor 54, the absolute value of the force exerted on diaphragm 64 by plunger 26 varies in an inversely proportional manner with the absolute value of the vacuum level. In other words, larger absolute values of vacuum yield smaller absolute values of force exerted by plunger 64, and smaller absolute values of vacuum yield larger absolute values of force exerted by plunger 64. This relationship may be calibrated so that when load cell 20 provides a force measurement to computer 22, computer 22 can calculate the vacuum level within cavity 60, aspiration manifold 56, and the eye.

As mentioned above, it is critical that sensor 54 accurately measure the vacuum within aspiration manifold 56 of cassette 14. It has been discovered that the accuracy of sensor 54 is largely dependent on the material properties and geometry of diaphragm 64. It has been further discovered that the thickness of diaphragm 64 is particularly important to the accuracy of sensor 54. Given the fact that this thickness is very small (e.g. on the order of 0.003 inches), such diaphragms may be somewhat challenging to manufacture to exactly the desired thickness.

The following describes the preferred procedure for insuring the accuracy of sensor 54 prior to surgery. Cassette 14 is inserted into cassette receiving area 16 of console 12. Computer 22 rotates linear stepper motor 18 so that load cell 20 just begins to provide a measurement to computer 22 of the force exerted by plunger 26 against diaphragm 64 ("$F_{plunger}$"). Computer 22 then rotates linear stepper motor 18 back 1 step. This plunger displacement is defined as "$D_0$". The linear displacement of plunger 26 beyond $D_0$ is equal to the displacement of diaphragm 64 by plunger 26, is a function of the rotation of linear stepper motor 18, and is defined as "D". Computer 22 then rotates linear stepper motor 18 in a step by step fashion until $F_{plunger}$ equals $F_{preload}$. Load cell 20 measures $F_{plunger}$ for each step and provides this force to computer 22. Computer 22 stores the value for D and the associated value of $F_{plunger}$ for each step. Computer 22 also compares the measured value of $F_{plunger}$ to the desired value of $F_{plunger}$ for each value of D. If the measured value of $F_{plunger}$ is not within a pre-defined tolerance of the desired value of $F_{plunger}$, computer 22 signals the surgeon via console 12 that the pressure sensor is defective and to insert a new cassette. Computer 22 may also prevent any surgical procedure due to the defective pressure sensor. If the measured value of $F_{plunger}$ is within the pre-defined tolerance of the desired value of $F_{plunger}$ for all values of D, the surgical procedure may proceed.

Figure 5:
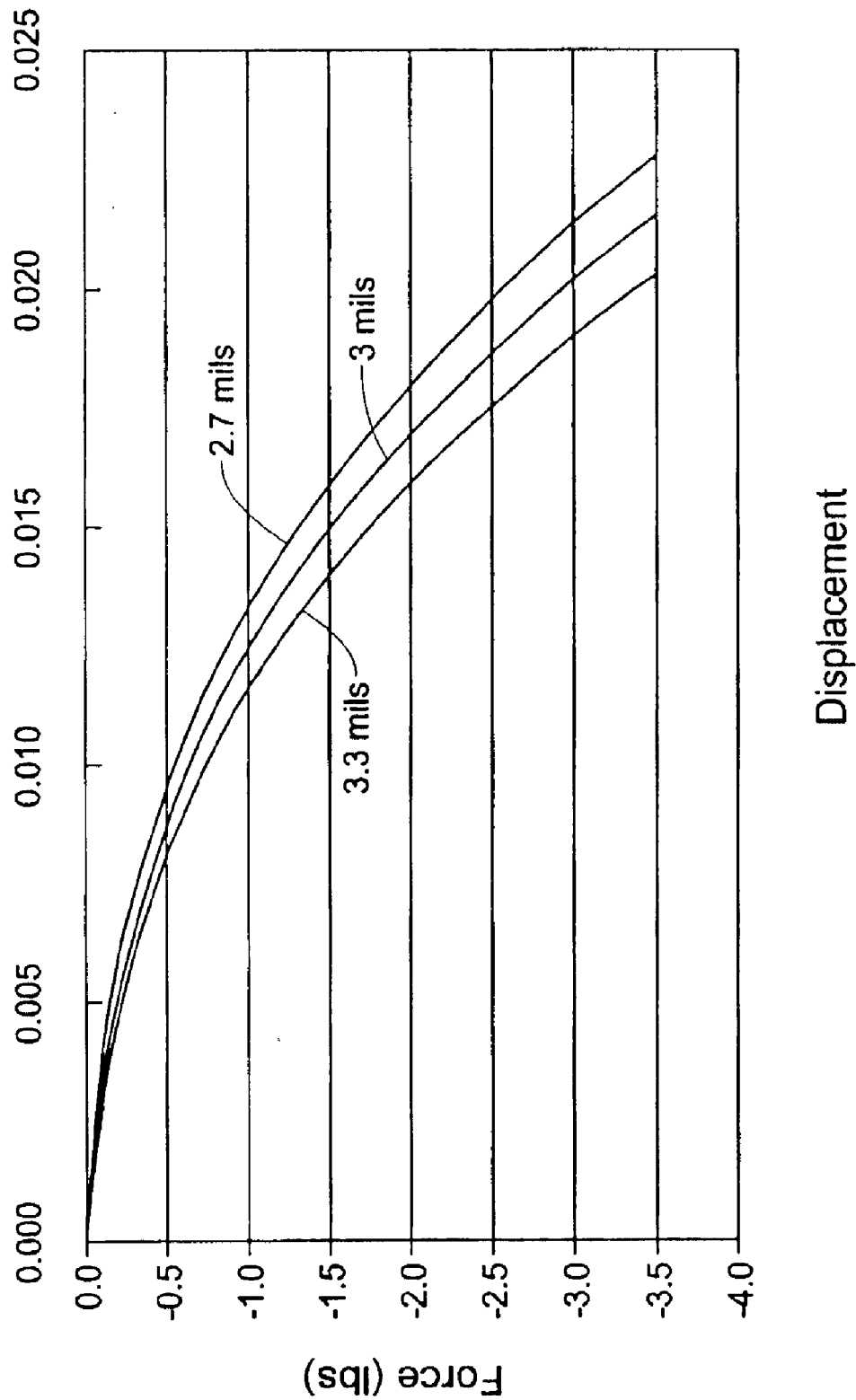
FIG. 5. is the preferred force versus displacement curve for the diaphragm of the sensor of FIGS. 2–3.

FIG. 5 shows the preferred force $F_{plunger}$ vs. displacement D curves for three diaphragms 64, the preferred diaphragm 64 made of 17-7 stainless steel, having a diameter of about 0.996 inches (not including rim 66), and a thickness of 0.003 inches; a diaphragm 64 having the above-described characteristics of the preferred diaphragm 64 but having a thickness of 0.0027 inches; and diaphragm 64 having the above-described characteristics of the preferred diaphragm 64 but having a thickness of 0.0033 inches. The three curves may be generated from actual operation of such diaphragms 64 in surgical console 12, or using a conventional finite element modeling package. The "0.003 inch" curve (or its mathematical equivalent) may be utilized to define the desired value of $F_{plunger}$ utilized by computer 22 when testing pressure sensor 54 as described above. Information from the "0.0033 inch" and "0.0027 inch" curves (or their mathematical equivalents) may be utilized to define the tolerances for the desired value of $F_{plunger}$ utilized by computer 22 when testing pressure sensor 54 as described above. Of course, different tolerance curves may be generated for different diaphragms 64 or different applications of cassette 14, if desired.

From the above, it may be appreciated that the present invention provides a simple and reliable apparatus and method of insuring the accuracy of a non-invasive pressure sensor of a surgical cassette. The present invention is illustrated herein by example, and various modifications may be made by a person of ordinary skill in the art. For example, computer 22 may generate a force $F_{plunger}$ versus displacement D curve for a given diaphragm 64 for the entire range of values of D, and then compare this curve to the "tolerance" curves in a batch mode rather than comparing each measured value of $F_{plunger}$ to see if it is within the pre-defined tolerance at the time its measured, as described above. As another example, $F_{plunger}$ may be measured at intervals of a pre-defined number of steps of linear stepper motor 18 instead of at each step of linear stepper motor 18 as described above.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A method of determining the accuracy of a pressure sensor in a surgical cassette, comprising the steps of:
   providing a surgical cassette having a pressure sensor, said pressure sensor having a diaphragm;
   providing a surgical console with a cassette receiving area;
   disposing said cassette in said cassette receiving area;
   displacing said diaphragm a pre-defined amount of displacement;

measuring a force exerted on said diaphragm by said displacing step; and determining an accuracy of said pressure sensor by comparing said force measured in said measuring step to a pre-defined force for said pre-defined amount of displacement.

2. The method of claim 1 further comprising the step of providing information to a user of said surgical console when said force measured in said measuring step is not within a pre-defined tolerance of said pre-defined force.

3. The method of claim 1 further comprising the step of preventing a surgical procedure when said force measured in said measuring step is not within a predefined tolerance of said pre-defined force.

4. The method of claim 1 wherein:

said surgical console comprises a linear actuator having a plunger and a load cell operatively coupled to said plunger, said displacing step comprises displacing said diaphragm with said plunger of said linear actuator; and said measuring step comprises measuring said force exerted on said diaphragm by said plunger with said load cell.

5. The method of claim 4 wherein said cassette has an aspiration manifold, and said diaphragm is in fluid communication with said aspiration manifold.

* * * * *